United States Patent

Hohla

[11] Patent Number: 5,891,132
[45] Date of Patent: *Apr. 6, 1999

[54] DISTRIBUTED EXCIMER LASER SURGERY SYSTEM

[75] Inventor: Kristian Hohla, Vaterstetten, Germany

[73] Assignee: Chiron Technolas GmbH Opthalmologische Systeme, Germany

[*] Notice: This patent issued on a continued prosecution application filed under 37 CFR 1.53(d), and is subject to the twenty year patent term provisions of 35 U.S.C. 154(a)(2).

[21] Appl. No.: 656,855

[22] Filed: May 30, 1996

[51] Int. Cl.$^6$ .................................................. A61F 9/00
[52] U.S. Cl. .................................................. 606/5; 606/10
[58] Field of Search .................................. 606/4, 5, 6, 10, 606/11, 12

[56] References Cited

U.S. PATENT DOCUMENTS

| | | |
|---|---|---|
| 4,554,917 | 11/1985 | Tagnon . |
| 4,665,913 | 5/1987 | L'Esperance, Jr. . |
| 4,669,466 | 6/1987 | L'Esperance . |
| 4,721,379 | 1/1988 | L'Esperance . |
| 4,729,372 | 3/1988 | L'Esperance, Jr. . |
| 4,732,148 | 3/1988 | L'Esperance, Jr. . |
| 4,840,175 | 6/1989 | Peyman . |
| 4,848,340 | 7/1989 | Bille et al. .................. 606/5 |
| 4,856,513 | 8/1989 | Muller . |
| 4,881,808 | 11/1989 | Bille et al. . |
| 4,901,718 | 2/1990 | Bille et al. . |
| 4,902,122 | 2/1990 | Azema et al. . |
| 4,902,123 | 2/1990 | Yoder, Jr. . |
| 4,907,586 | 3/1990 | Bille et al. .................. 606/5 |
| 4,911,711 | 3/1990 | Telfair et al. . |
| 4,923,467 | 5/1990 | Thompson . |
| 4,941,093 | 7/1990 | Marshall et al. . |
| 4,973,330 | 11/1990 | Azema et al. . |
| 4,993,826 | 2/1991 | Yoder, Jr. . |
| 4,994,058 | 2/1991 | Raven et al. . |
| 4,998,819 | 3/1991 | Labinger et al. . |
| 5,049,147 | 9/1991 | Danon .................. 606/4 |
| 5,098,426 | 3/1992 | Sklar et al. .................. 606/4 |
| 5,106,183 | 4/1992 | Yoder, Jr. . |
| 5,137,530 | 8/1992 | Sand . |
| 5,147,352 | 9/1992 | Azema et al. . |
| 5,196,006 | 3/1993 | Klopotek et al. .................. 606/4 |
| 5,295,989 | 3/1994 | Nakamura . |
| 5,374,265 | 12/1994 | Sand . |
| 5,395,356 | 3/1995 | King et al. .................. 606/5 |
| 5,404,884 | 4/1995 | Lempert . |
| 5,460,627 | 10/1995 | O'Donnell, Jr. . |
| 5,569,238 | 10/1996 | Shei et al. .................. 606/4 |
| 5,591,185 | 1/1997 | Kilmer et al. .................. 606/166 |

FOREIGN PATENT DOCUMENTS

| | | |
|---|---|---|
| 111060 | 9/1983 | European Pat. Off. . |
| 151869 | 11/1984 | European Pat. Off. . |
| 191688 | 1/1986 | European Pat. Off. . |
| 207648 | 6/1986 | European Pat. Off. . |
| 224322 | 9/1986 | European Pat. Off. . |
| 209992 | 1/1987 | European Pat. Off. . |
| 257836 | 7/1987 | European Pat. Off. . |
| 274205 | 11/1987 | European Pat. Off. . |
| 247260 | 3/1988 | European Pat. Off. . |
| 299836 | 6/1988 | European Pat. Off. . |
| 346116 | 6/1989 | European Pat. Off. . |
| 503802 | 9/1992 | European Pat. Off. . |
| 628298 | 5/1994 | European Pat. Off. . |
| 721129 | 1/1996 | European Pat. Off. . |
| WO9216141A | 10/1992 | WIPO . |
| 9407447 | 4/1994 | WIPO .................. 606/4 |
| WO9611655A | 4/1996 | WIPO . |

*Primary Examiner*—Max Hindenburg
*Assistant Examiner*—Sonya Harris-Ogugua
*Attorney, Agent, or Firm*—Pravel, Hewitt & Kimball

[57] ABSTRACT

A distributed system is provided for controlling excimer laser eye surgery. A topography system, a computer system, and an excimer laser eye surgery system are provided, with the topography system providing profile data to the computer system, and the computer system calculating and providing an ablation shot pattern to the excimer laser eye surgery system. At least the computer system and the excimer laser eye surgery system are located remotely, and the excimer laser eye surgery system can receive data from more than one computer system and more than one topography system. This allows for better utilization of resources.

23 Claims, 5 Drawing Sheets

DISTRIBUTED EXCIMER LASER SURGERY SYSTEM

BACKGROUND OF THE INVENTION

1. Field of the Invention

The invention relates to excimer laser eye surgery systems, and more specifically to distributed topography, treatment creation, and excimer laser system.

2. Description of the Related Art

Excimer laser eye surgery systems are becoming a more often used system for correcting vision. From eye glasses to radial keratotomy, ophthalmic surgery has now progressed to a point where the surface of the eye is actually reshaped using cold light laser ablation provided by excimer lasers, typically argon fluoride lasers operating at around 193 nanometers. These lasers are even used to reshape the stromal tissue underneath the surface of the eye in a laser in situ keratomileusis technique patented by Gholam Peyman in U.S. Pat. No. 4,840,175, which is hereby incorporated by reference.

These techniques start with the uncorrected profile of the eye, and then ablate the eye using various small or large beam techniques, or aperture techniques, to reprofile the surface into a desired, corrected profile. The amount of correction is determined by a variety of methods, but for myopia, for example, given the starting curvature of the eye and the amount of dioptric correction needed, equations are well known which specify the amount of tissue that must be removed from each point on the surface of the eye. These equations are found, for example, in assignee's PCT patent application serial no. PCT/EP93/02667, as well as the U.S. counterpart to that application, Ser. No. 08/338,495, filed Nov. 16, 1994, which is hereby incorporated by reference. Similar equations are known for the amount of tissue necessary for removal to correct for hyperopia and astigmatism.

Before relying on these equations, however, the actual curvature of the eye must be determined. This is done using a number of techniques. The patient's visual acuity can be determined through eye exams. The actual shape of the surface of the eye can be determined, for example, using a topography system. These topography systems can be either manual or computerized, and the latter can provide a point-by-point representation of the curvature of the eye, for example, in the form of an axial curvature, the instantaneous or true local curvature, or the absolute height.

Typically, based on these curvatures and the patient's visual acuity, the doctor programs into an excimer laser surgery system an amount of positive or negative dioptric correction (depending on whether the correction is for hyperopia or myopia) and an angle of the cylinder of astigmatism, if any, along with the amount of dioptric correction necessary for the astigmatism. Software within the excimer system itself then calculates the necessary shot pattern and that pattern is executed on the surface of the patient's eye.

Such a system, however, places limits on the different types of vision defects that can be corrected. Further, it would be desirable to more efficiently use expensive resources in such systems.

SUMMARY OF THE INVENTION

According to the method and apparatus of the invention, vision correcting excimer laser shot patterns are developed and applied in a distributed system, where a topography system provides corneal profile data, a computer system develops an ablation shot pattern or a course of excimer laser shots for correction of the cornea, and an excimer laser system fires that ablation shot pattern. At least one of the components of this system, however, is physically located away from the other two components.

This system provides in one embodiment multiple topography stations, each connected to a computer for creating an ablation shot profile. The data is then transmitted to a physically remote excimer laser surgery system for later executing the ablation treatment pattern.

In this way, topography systems, which are widely used for a variety of ophthalmic techniques, can be utilized at various locations throughout a region. Then, the data from those topography systems is then transmitted to a computer system, on which the doctor develops a treatment pattern for an excimer laser system. That pattern is then transmitted to a centralized location where the patient can go and receive treatment from an excimer laser system. This allows more efficient utilization of resources, as each doctor need not acquire his or her own excimer laser surgery system.

Further, the station for developing the ablation shot treatment pattern allows a physician to automatically generate treatment patterns resulting in various dioptric overall correction of the eye, as well as a cylinder axis of and degree of astigmatism correction. Further, however, it allows the doctor to provide for non-standard treatment, using manually or semi-manually placed shots. The treatment pattern can then be simulated on the profile of the eye received from the topography system, and the doctor can examine the results. In this way, the doctor can correct for irregular abnormalities, such as hot spots, curved and irregular astigmatism patterns, etc., and see the results of those corrections in a real time simulation. The shot pattern is then later applied to the patient at the remote location.

Further, the physician can do this both away from the topography system and away from the excimer laser system. The doctor could, for example, take a number of treatment patterns home, along with the corresponding corneal topography data, and prepare the appropriate ablation shot pattern after hours on a personal computer.

The data can be transmitted between these various components in a variety of methods, including over a computer network, over a telecommunications link, or through diskette or other removable media.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
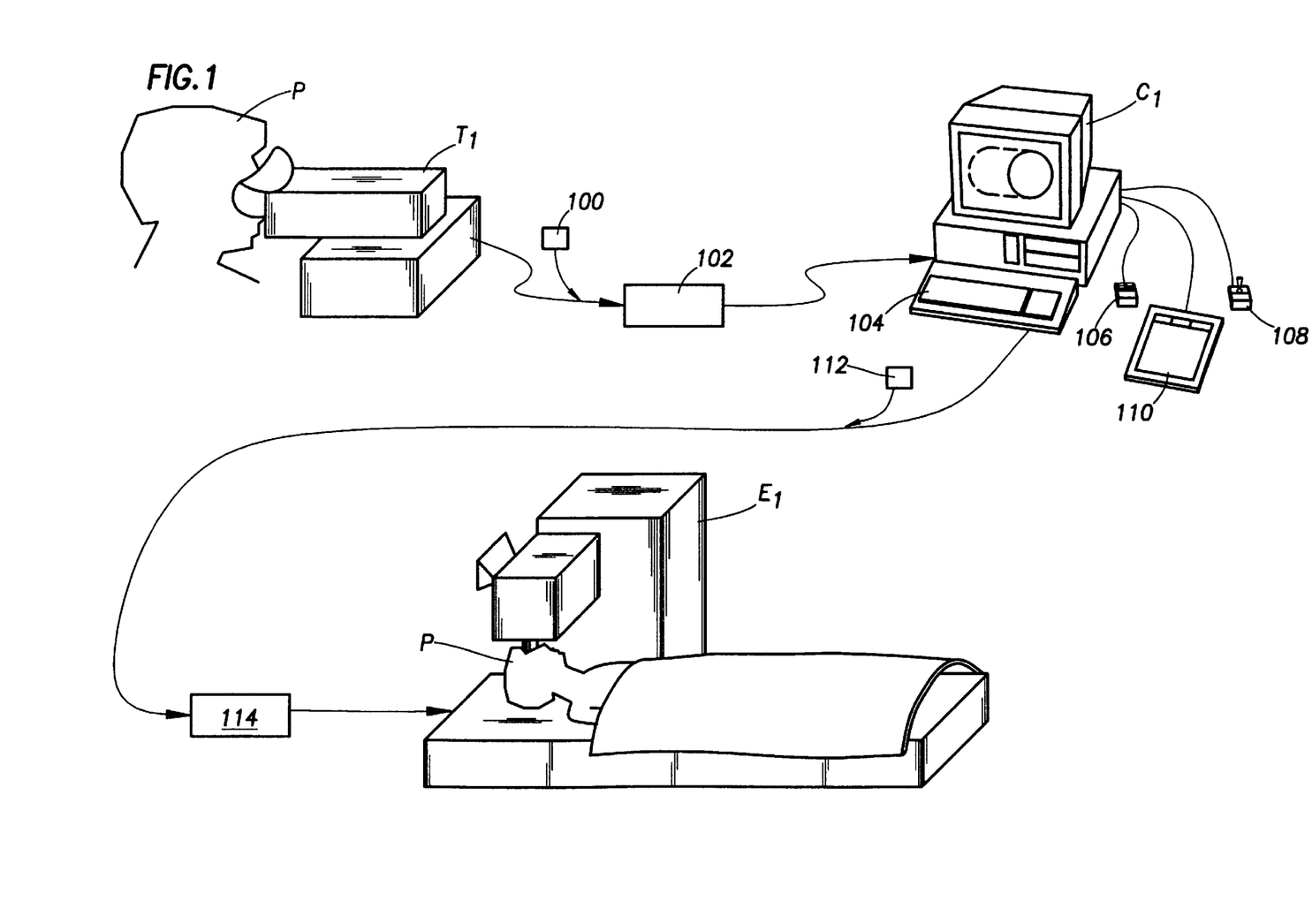
FIG. 1 is a block diagram illustrating the interrelationship of the components of the excimer laser eye surgery system according to the invention.

Turning to FIG. 1, shown is a block diagram illustrating the interrelationship of the components according to the system. Specifically, a topography system $T_1$, a computer system $C_1$, and an excimer laser eye surgery system $E_1$ are all coupled to form the distributed eye surgery system according to the invention. The topography system $T_1$, could be a wide variety of topography systems, but is preferably a System 2000 by Eyesys. In any case, the topography system $T_1$ is preferably computerized and provides a data file in the form of a point representation of, for example, fifteen points along each meridian between 0° and 360° at five-degree increments. The point representation could show axial curvature, which represents the curvature at each point corresponding to a sphere on the same spherical axis of the eye; local curvature, in which a sphere tangent to the local curvature may not be axially aligned with the spherical axis of the eye; or absolute height, which is height off of a plane or off of a sphere. The data files produced by the variety of topographic systems are well known, and adaptation to any particular data format would be readily accomplished by one skilled in the art.

This topography system $T_1$ is used to obtain topographic data from a patient P. Topographic data, illustrated by a block 100, is transmitted to the computer system $C_1$. This transmission can be accomplished by a variety of transmission techniques, illustrated by the block 102. For example, data can be carried in the form of a diskette or other removable media, can be transmitted over a local network, can be transmitted over a serial or parallel link, can be transmitted via a telecommunications link or can be transmitted over a wide area network. It will be readily appreciated that the type of link is adaptable to and dependent on the implementation of various systems involved. In any case, the profile data 100 is received by the computer system $C_1$. The computer system $C_1$ is preferably a personal computer, such as a personal computer compatible with the IBM PC by International Business Machines. Preferably, it includes a fairly high-powered processor, such as the Pentium Processor by Intel Corporation. The computer system $C_1$ can include a variety of input/output devices, such as a keyboard 104, a mouse 106, a joy stick 108, and a digitizer 110. These various input/output devices are used to allow a physician to interact with the computer program to create an ablation shot pattern illustrated by the block 112.

As is discussed below in conjunction with FIGS. 5 and 6, the computer system $C_1$ preferably runs a computer program in which an initial correction ablation shot pattern is created based on the received topographic profile data 100 from the topography system $T_1$ as well as visual acuity data manually entered by the doctor. For example, the doctor would enter the degree of visual acuity dioptric correction required, such as −5.00 for a typical myopic patient, and could enter an axis of astigmatism correction and a degree of astigmatism correction if desired. Then, based on the topographic data, the program in the computer system $C_1$ calculates an ablation shot profile for a desired size treatment area, which could further incorporate, for example, transition zones, dithering, polishing, or a wide variety of other techniques known to the art. Further detail of such techniques are found in assignee's U.S. patent application Ser. Nos. 08/338,495, filed Nov. 16, 1994, and 08/324,782, filed Oct. 18, 1994, which are hereby incorporated by reference. Further, based on the corneal profile data 100, the computer system $C_1$ can adjust the axis of the astigmatism correction, as well as the degree of astigmatism correction. The could then verifies the results of this automatic calculation on the actual cornea by perform a simulation, in which the profile of the eye according to the profile data 100 is "ablated" by the software in the computer system $C_1$, with the resulting profile appearing on the monitor of the computer system $C_1$. Based on the results of this simulation, the doctor can perform further, manual shot placement to correct, for example, for "hot spots," for irregular astigmatism, or other abnormal defects.

Once the doctor is satisfied with the results of the ablation shot pattern, the ablation shot pattern 112 is transmitted to the excimer laser eye surgery system $E_1$ via a second transmission link 114. This second transmission link 114 can be similar to the transmission link 102, including removable media, telecommunications, local or wide area network, or other types of transmission links for transmitting digital data from one location to another.

The excimer laser eye surgery system $E_1$ can be any of a number of excimer laser eye surgery systems of a variety of types. Preferably, it is a Keracor 117 or a Keracor 217 by Chiron Technolas GmbH. These are fixed spot size excimer laser systems, but a variety of other types of systems could instead be used. For each system, the excimer laser eye surgery system $E_1$ receives the ablation shot pattern from the remote computer system $C_1$.

The patient P then travels to the location where the excimer laser eye surgery system $E_1$ is found. This could be a centralized eye surgery area in a hospital, for example, or a centralized clinic within a city. The ablation shot pattern 112 is then fired, correcting the vision of the patient P.

The patient P need not even have the surgery performed immediately, but could instead wait for the following day or days. Further, the doctor does not necessarily need to be present to perform the surgery, but it could instead be performed by a separate ophthalmologist.

Figure 2:
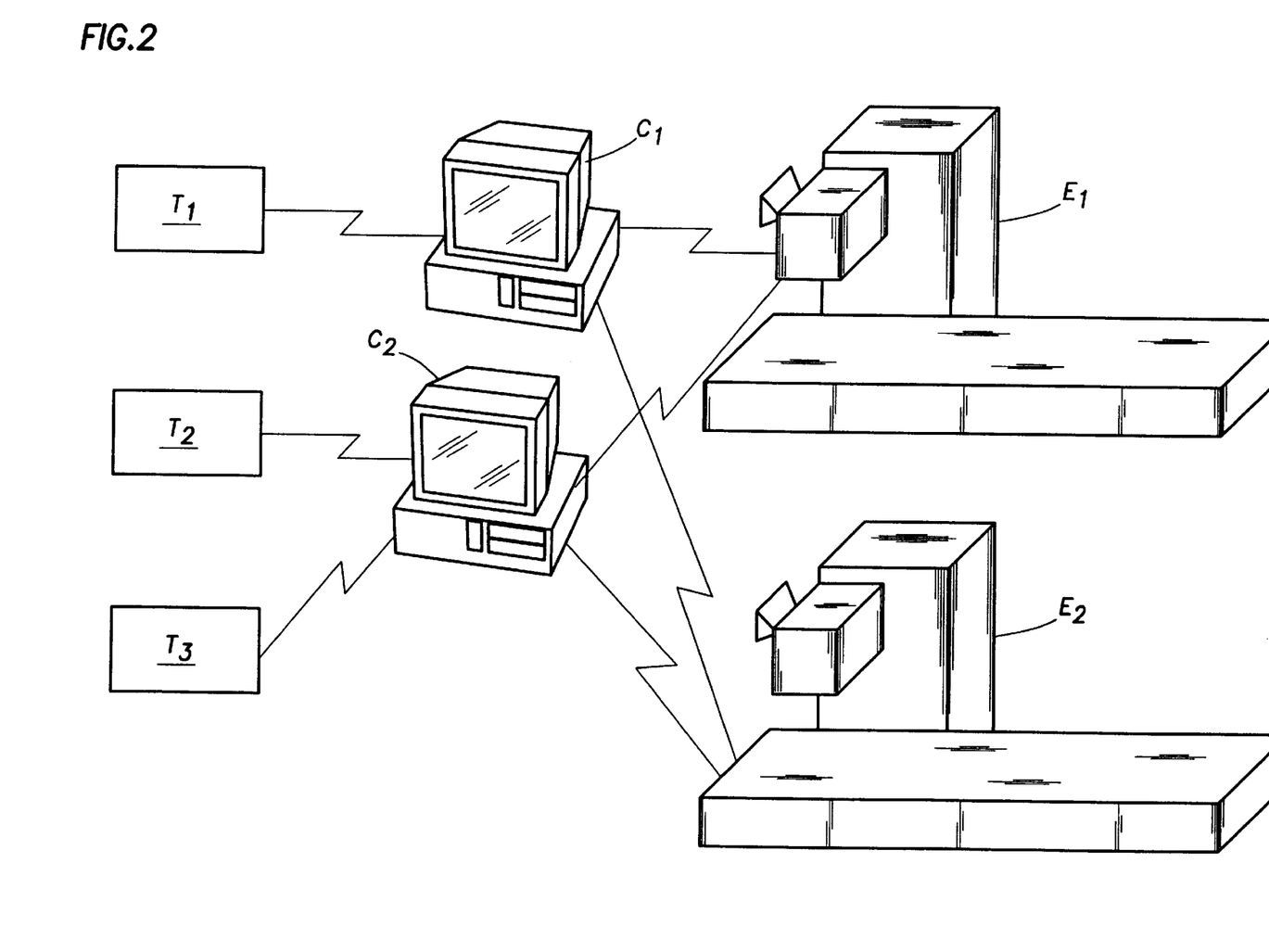
FIG. 2 is a block diagram illustrating the interrelationship of multiple components in an excimer laser eye surgery system according to the invention.
Figures 3, 4:
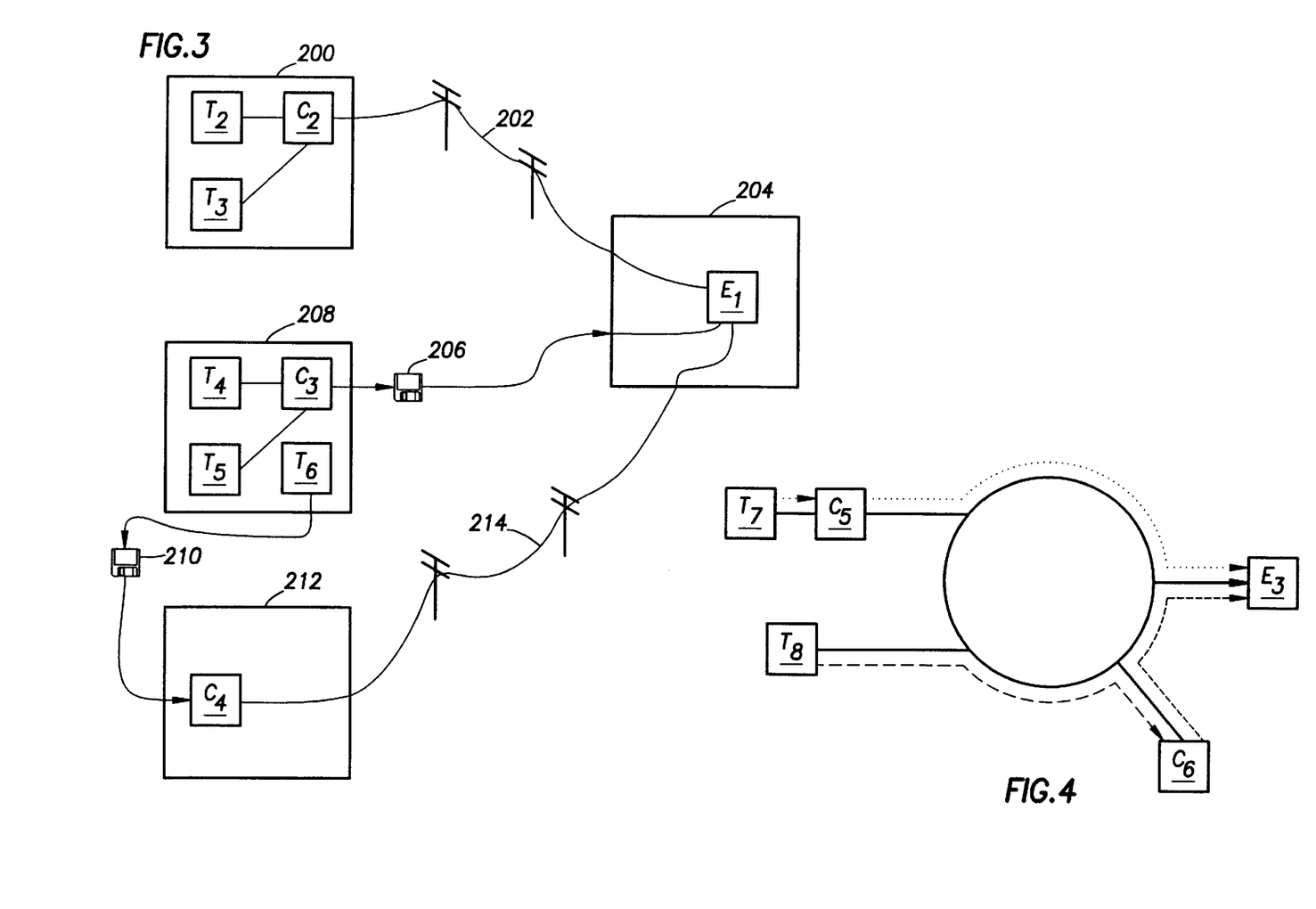
FIG. 3 is a block diagram illustrating physical locations and physical links between various components in an laser eye surgery system according to the invention.
FIG. 4 is a block diagram of a networked system according to the invention.

Advantages of the system become apparent with reference to FIG. 2, in which is illustrated how multiple topography systems, multiple computers, and multiple excimer laser eye surgery systems are linked to provide maximum utilization of resources. The topography system $T_1$, computer system $C_1$, and excimer laser eye surgery system $E_1$ are shown, in addition to topography systems $T_2$ and $T_3$, which are both coupled to a computer system $C_2$, which is coupled to both the excimer laser eye surgery system $E_1$, and a second excimer laser eye surgery system $E_2$. As is appreciated from this block diagram, the profile data 100 from the topography system $T_1$ is provided to the computer system $C_1$, and that data can then be transmitted to either of a more convenient excimer laser eye surgery system $E_1$ or $E_2$. Similarly, multiple topography systems $T_2$ and $T_3$ can provide their data to the computer system $C_2$, which in turn can transmit its data to a more convenient of the two excimer laser eye surgery systems $E_1$ or $E_2$. Turning to FIG. 3, shown is a typical implementation of such a system. A building or location 200 houses the computer system $C_2$ and the topography systems $T_2$ and $T_3$. This could be an eye clinic in which topography systems $T_2$ and $T_3$ are used to acquire profile data corresponding to the profile data 100, and the computer system $C_2$ receives that profile data over a transmission link corresponding to the transmission link 102. In the illustrated case, the computer system $C_2$ then transmits an ablation shot pattern corresponding to the ablation shot pattern 102 over a telephone line 202. So, in this case, the telephone line 202 corresponds to a particular implementation of the second transmission link 114. The ablation shot pattern 102 is then received at a second building or location 204, in which is located the excimer laser eye surgery system $E_1$.

But the excimer laser eye surgery system $E_1$ is not restricted to a single topography system and a single computer system. The excimer laser eye surgery system E, also receives an ablation shot pattern via a diskette 206 from a computer $C_3$ located in yet another building or location 208. Also in that building or location 208 are further topography systems $T_4$ and $T_5$. The building or location 208 also includes another topography system $T_6$ which in this case is independent and provides profile data on diskette, and allowing physicians to take profile data corresponding to the profile data 100 home on diskettes, such as a diskette 210. While the physician is home 212, he or she can use a personal computer $C_4$ to create ablation shot patterns corresponding to the ablation shot pattern 112, and that data is then transmitted over a telephone link 214 to the excimer laser eye surgery system $E_1$.

This implementation makes it apparent that the distributed system according to the invention permits better utilization of resources than previous systems. An excimer laser eye surgery system is typically very expensive and very specialized, being used for photorefractive keratectomy, phototherapeutic keratectomy, and laser in situ keratomileusis. The amount of time for a treatment is typically fairly short, usually less than an hour. Generally, more time is necessary to determine the degree of correction required and to create the ablation profiles for performing the correction.

By using the distributed system according to the invention, the excimer laser eye surgery system E is more efficiently utilized because the ablation profiles are created separately by various topography systems T for providing data (again, a fairly quick procedure) and then personal computers C being used to determine the desired ablation treatment pattern. Then, the patient goes to a centralized location of where the excimer laser eye surgery system E is provided.

This also permits ophthalmic surgeons to pool their resources. Rather than each purchasing their own excimer laser eye surgery system, they simply use a topographic system $T_1$ which is a common instrument with wide application, along with a personal computer C, which, again, virtually every modern physician has access. Then, the excimer laser eye surgery system E is used by all, perhaps for a user fee.

FIG. 4 illustrates an alternative embodiment useful, for example, in a hospital setting. Here, a network N is used for both the transmission link 102 and the transmission link 114 of FIG. 1. For example, an excimer laser eye surgery system $E_3$ is coupled to a local network, along with topography systems $T_7$ and $T_8$, and computer systems $C_5$ and $C_6$. In this configuration, the topography system $T_7$ is coupled to the computer system $C_5$, through, for example, a direct serial link, a subnetwork, or diskette, and then the computer system $C_5$ is coupled to the excimer laser eye surgery system $E_3$ over the network N. Also, the topography system $T_g$ is coupled to the computer system $C_6$ (or, in fact, to the computer system $C_5$) providing the corneal profile data, and then the computer system $C_6$ provides the ablation shot pattern to the excimer laser eye surgery system $E_3$. In this way, a local network is used to connect many topography systems T and computer systems C to a single excimer laser eye surgery system $E_1$ allowing the shot patterns to be calculated at locations separate and apart from the excimer laser eye surgery system $E_3$. For example, the excimer laser eye surgery system $E_3$ could be located in a clean room, while the other portions are not. Clean rooms are expensive, so this additionally allows a more efficient utilization of resources.

Figure 5:
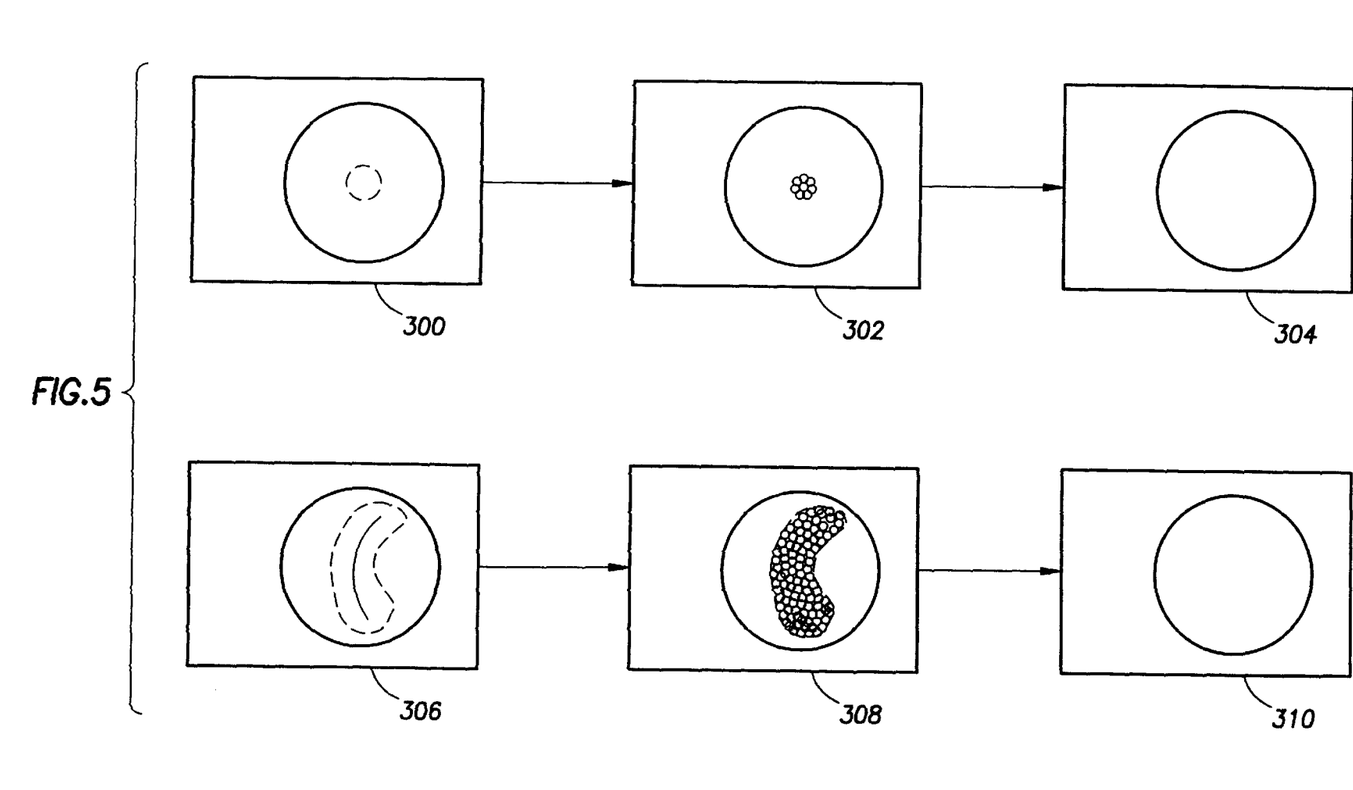
FIG. 5 shows illustrations of display screens for providing manual correction of an ablation profile according to the invention.

Turning to FIG. 5, shown are typical screens provided by the computer system $C_1$ in the correction of corneal abnormalities. The screen typically shows corneal profile data using varying color, as well as cross sections. To illustrate, a screen 300 illustrates a central island, for example through a center section that has a color indicating a deviation from the desired profile for the degree of correction necessary. The physician can then apply a series of shots as illustrated in screen 302 to correct for that central island. This could be done in a variety of methods, such as through the keyboard 104, the mouse 106, the joy stick 108, or the digitizer 110. The physician then runs a simulation to determine the resulting curvature and repeats as necessary until he yields the desired corneal profile 304. The screen 306 illustrates a curved astigmatism, again which is apparent as a different color on the screen. In step 308, the physician has manually placed a series of shots in the curved astigmatism (typically with more towards the central axis than towards the periphery) and has repeatedly run the simulation until the result of the treatment on the actual profile data is a desired corneal curvature illustrated as in the screen 310.

It will be appreciated that the exact software for creating the ablation shot pattern may differ depending on the style of excimer laser eye surgery system E. For example, in a small beam scanning system, a physician may variously designate areas from which a layer is to be removed, and then the computer system would calculate automatically the shot pattern necessary to remove that pattern In a large beam variable spot size system, the physician may have control over both the spot size and the shot location.

Figure 6:
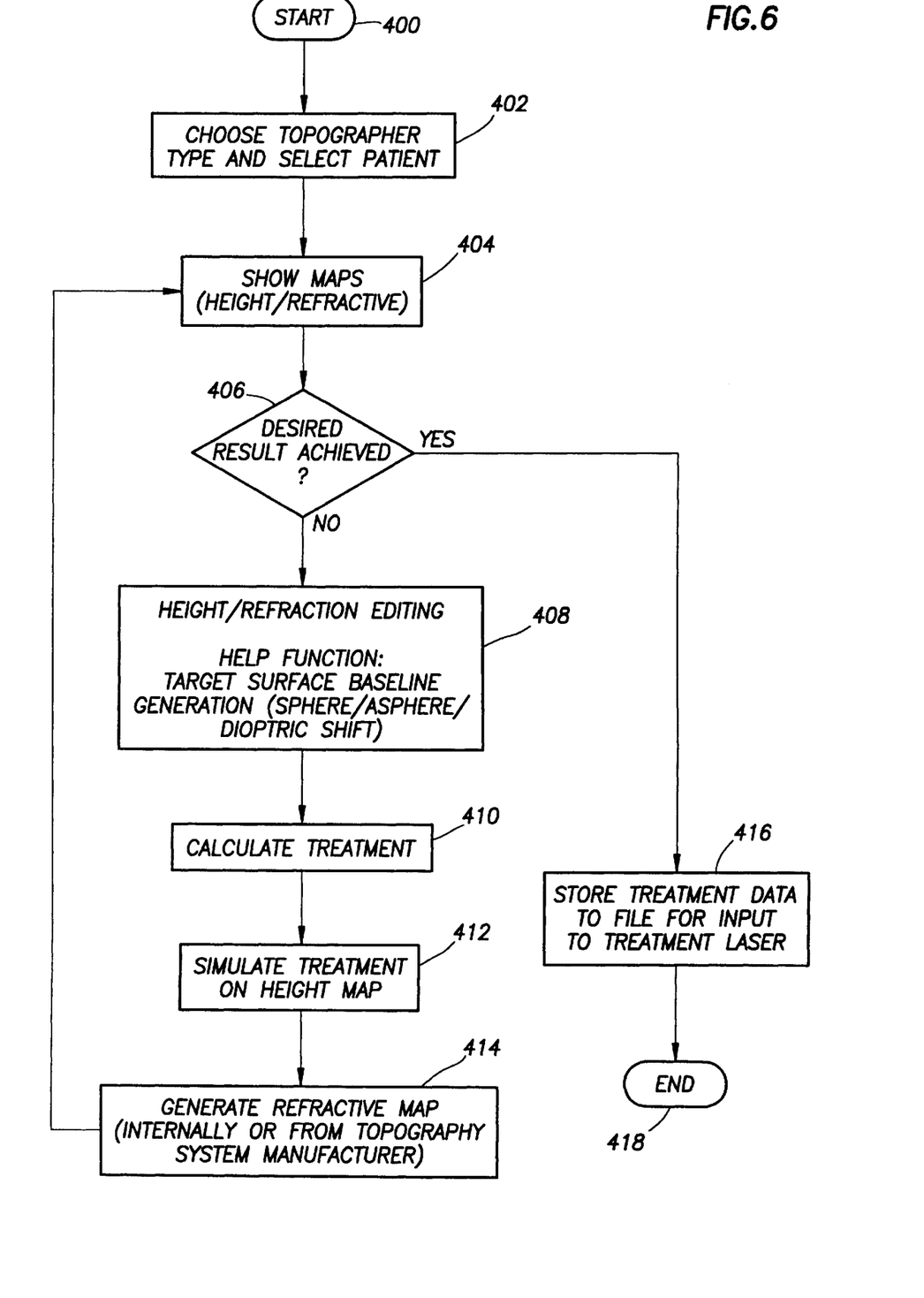
FIG. 6 is a flow diagram illustrating operation of a computer program on a computer in a system according to the invention.

Turning to FIG. 6, shown is a flow diagram for providing the physician controlled treatment pattern generation on the computer system C according to the invention. The routine 400 begins at step 402, where the physician selects both the type of topography system used and the patient data. The patient data has been previously provided, for example, as the profile data 100 from the topography system T over the transmission link 102. Proceeding to step 404, maps are displayed on the screen illustrating true height and refractive deviation from a desired sphere, or a deviation from a desired curvature. These maps are typically displayed using various color intensities to illustrate more or less deviation from the desired result.

Proceeding to step 406, it is determined whether the desired result has been achieved. This would be true if the results of the treatment pattern would yield the desired curvature. Generally, on the first time through this loop beginning at step 406, the desired result has not been achieved, because no shots have even tentatively been applied. Proceeding to step 408, the physician is given the opportunity to create a treatment pattern. Typically, a physician would not reasonably be able to create an effective treatment pattern totally by hand. Therefore, at step 408, the computer system C gives the physician the option of letting computer system C find a basic target surface which the physician can take as the basis for his hand fine turning. For example, he can choose a spherical model, an aspherical model, or an input refractive change. The spherical model shows how closely a sphere fits to the original surface. An aspherical model provides varying degrees of curvature across the surface. A refractive change would simply the inner dioptric degree of correction.

Once this base line surface is generated, control proceeds to step 410, where the computer system C calculates the desired treatment pattern. This involves creating the shots necessary to correct according to the target base line generated at step 408. Then proceeding to 412, that calculated treatment pattern is simulated onto patient P's corneal profile height map.

Then proceeding to step 414, a refractive map is created from that height map. The refractive map generation routines are typically provided by the manufacturer, or could be performed on an internal model. This refractive map allows the physician to see how optically accurate the current treatment is. Control then loops to step 404, where the height and refractive maps are again displayed. Proceeding to step 406, it is then determined whether the desired result has been achieved. (Of note, this can be done either manually through physician approval, or through physician approval in conjunction with a determination of average error of refractive correction.) Assuming that the desired result has not been achieved, control again proceeds to step 408. This time, the physician will wish to fine tune by providing more or less correction in certain spots. Referring back to FIG. 5, that figure illustrates the types of fine tuning the physician can perform to achieve a better refractive pattern.

The physician repeats these steps beginning at step 406 until the desired result is achieved. At that point, control proceeds to step 416, where the treatment data is stored to a file for input to the excimer laser eye surgery system E. Control then proceeds to step 416 where the routine ends. At this point, the data would be transmitted over the second transmission link 114 or its equivalent.

It will be appreciated that the exact technique and program for allowing physician correction is not critical. But it should be executable independently of the excimer laser eye surgery system E, so that the data can then be transmitted to a centralized excimer laser eye surgery system E.

It will be appreciated that this distributed system allows more efficient utilization of topography systems, computer systems, and excimer laser eye surgery systems. Further, it provides for a greater degree of control and modification of the ablation shot pattern to be applied to the patent P's eyes.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

I claim:

1. A method of providing control of a laser eye surgery system, comprising the steps of:

(a) determining the profile of a cornea with a topography system at a first location, (b) generating a digital data file corresponding to the profile of the cornea;

(c) generating on a computer system at a second location from the digital data file an ablation shot pattern file for a course of laser shots corresponding to a desired correction for the cornea;

(d) transmitting the ablation shot pattern file to a control unit of a laser system at a third location, wherein the third location is in a physically different vicinity than the first location and the second location and wherein the computer system is a physically distinct unit physically remote from the laser systems, such that a shot pattern file for a course of the laser shots could be created on the computer system at the second location while the laser system is providing a laser treatment at the third location;

(e) receiving the transmitted ablation slot pattern file into the control unit of the laser system at the third location as a received ablation shot pattern;

(f) directing the laser system via the control unit to fire a shot pattern corresponding to that found in the received ablation shot pattern.

2. The method of claim 1 further comprising the steps of:

(g) determining the profile of a second cornea with a second topography system at a fourth location;

(h) generating a second digital data file corresponding to the profile of the second cornea;

(i) generating at a fifth location from the second digital data file a second ablation shot pattern for a second course of laser shots corresponding to a second desired correction for the second cornea;

(j) transmitting the second ablation shot pattern file to the laser system at the third location, wherein the third location is in a physically different vicinity than the fourth location and the fifth location;

(k) receiving the transmitted second ablation shot pattern file as the received ablation shot pattern; and (l) performing step (f) after step (k).

3. The method of claim 1, wherein step (c) further comprises the steps of:

(c1) displaying on a display screen a representation of the cornea profile corresponding to the digital data file after a treatment according to a first stored course of shots;

(c2) providing manual physician input altering the course of shots and storing the results as the stored course of shots;

(c3) repeating steps (c1) and (c2) until the physician is satisfied with the stored course of shots as corresponding to the desired correction; and (c4) after step (c3), providing the ablation shot pattern file based on the stored course of shots.

4. The method of claim 3, wherein step (c) further comprises the steps of:

(c5) before step (c1) automatically calculating an initial course of shots from the digital data file and saving that as the stored course of shots before proceeding to step (c1).

5. The method of claim 3, wherein in step (c), the physician manually corrects for a central island.

6. The method of claim 3, wherein in step (c), the physician manually corrects for astigmatism with a curved axis.

7. The method of claim 4, wherein step (c5) further comprises the step of automatically calculating a myopia correcting initial course of shots.

8. The method of claim 4, wherein step (c5) further comprises the step of automatically calculating a hyperopia correcting initial course of shots.

9. The method of claim 4, wherein step (c5) further comprises the step of automatically calculating astigmatism correcting initial course of shots.

10. The method of claim 1, wherein step (d) further comprises the step of:

writing the ablation shot pattern file onto a diskette, and wherein step (e) further comprises the step of:

reading the ablation shot pattern file from the diskette as the received ablation shot pattern file.

11. The method of claim 1, wherein step (d) further comprises the step of:
sending the ablation shot pattern file over a modem link, and wherein step (e) further comprises the step of:
receiving the ablation shot pattern file from the modem link as the received ablation shot pattern file.

12. The method of claim 1, wherein step (d) further comprises the step of:
sending the ablation shot pattern file over a network link, and wherein step (e) further comprises the step of:
receiving the ablation shot pattern file from the network link as the received ablation shot pattern file.

13. The method of claim 2, wherein step (j) further comprises the step of:
writing the ablation shot pattern file onto a diskette, and wherein step (k) further comprises the step of:
reading the ablation shot pattern file from the diskette as the received ablation shot pattern file.

14. The method of claim 2, wherein step (j) further comprises the step of:
sending the ablation shot pattern file over a modem link, and wherein step (k) further comprises the step of:
receiving the ablation shot pattern file from the modem link as the received ablation shot pattern file.

15. The method of claim 2, wherein step (j) further comprises the step of:
sending the ablation shot pattern file over a network link, and wherein step (k) further comprises the step of:
receiving the ablation shot pattern file from the network link as the received ablation shot pattern file.

16. A system for distributed control of a laser surgery system, the system comprising:
a topography system that provides profile data corresponding to the profile of the cornea of a patient;
a computer system with a program for developing an ablation shot pattern from the profile data;
a first data link between said topography system and said computer system for transmission of the profile data from said topography system to said computer system;
a laser eye surgery system having a control suit for directing a laser to fire a shot pattern corresponding to the ablation shot pattern; and
a second data link between said computer system and the control unit of said laser eye surgery system for transmission of the ablation shot pattern from said computer system to said laser eye surgery system;
wherein said laser eye surgery system is located in a physically different vicinity than said computer system said and wherein the computer system is a physical distinct unit physically remote from the laser system, such that an ablation shot pattern could be created on the computer system while the laser system is providing a laser treatment in the physically different vicinity.

17. The system of claim 16, wherein said laser eye surgery system is located in a clean room and said computer system is located outside of said clean room.

18. The system of claim 16, wherein said second data link is a telephone link.

19. The system of claim 16, wherein said second data link is a computer network.

20. The system of claim 16, wherein said second data link is a diskette.

21. The system of claim 16 further comprising:
a second topography system that provides second profile data corresponding to the profile of the cornea of a second patient;
a second computer system with a program for developing a second ablation shot pattern from the second profile data;
a third data link between said second topography system and said second computer system for transmission of the second profile data from said second topography system to said second computer system;
a fourth data link between said second computer system and said laser eye surgery system for transmission of the second ablation shot pattern from said second computer system to said laser eye surgery system, wherein said laser eye surgery system directs the laser to fire a shot pattern corresponding to the second ablation shot pattern.

22. The computer system of claim 21, wherein said second data link and said fourth data link are a single computer network.

23. The computer system of claim 16, wherein said computer system further includes:
a program for automatically developing a preliminary ablation shot pattern from the profile data; and
for allowing manual modification of the ablation shot pattern by a physician.

* * * * *